United States Patent
Seo et al.

(10) Patent No.: US 10,829,630 B2
(45) Date of Patent: Nov. 10, 2020

(54) SUPER ABSORBENT POLYMER

(71) Applicant: LG Chem, Ltd., Seoul (KR)

(72) Inventors: Sung Jong Seo, Daejeon (KR); Chang Sun Han, Daejeon (KR); Hyemin Lee, Daejeon (KR); Hyung Ki Yoon, Daejeon (KR)

(73) Assignee: LG Chem, Ltd. (KR)

( * ) Notice: Subject to any disclaimer, the term of this patent is extended or adjusted under 35 U.S.C. 154(b) by 74 days.

(21) Appl. No.: 15/770,359

(22) PCT Filed: Jan. 3, 2017

(86) PCT No.: PCT/KR2017/000055
§ 371 (c)(1),
(2) Date: Apr. 23, 2018

(87) PCT Pub. No.: WO2017/155196
PCT Pub. Date: Sep. 14, 2017

(65) Prior Publication Data
US 2018/0312680 A1    Nov. 1, 2018

(30) Foreign Application Priority Data

Mar. 11, 2016 (KR) .................. 10-2016-0029831
Aug. 18, 2016 (KR) .................. 10-2016-0104933

(51) Int. Cl.
*C08L 33/08* (2006.01)
*C08J 3/075* (2006.01)
*C08J 3/24* (2006.01)
*C08F 6/28* (2006.01)
*A61L 15/60* (2006.01)
*C08J 3/12* (2006.01)
*C08F 2/44* (2006.01)
*C08F 2/10* (2006.01)
*C08F 6/00* (2006.01)
*A61F 13/53* (2006.01)
*C08F 20/06* (2006.01)
*C08F 20/18* (2006.01)

(52) U.S. Cl.
CPC ............. *C08L 33/08* (2013.01); *A61L 15/60* (2013.01); *C08F 2/10* (2013.01); *C08F 2/44* (2013.01); *C08F 6/008* (2013.01); *C08F 6/28* (2013.01); *C08J 3/075* (2013.01); *C08J 3/12* (2013.01); *C08J 3/24* (2013.01); *C08J 3/245* (2013.01); *A61F 13/53* (2013.01); *A61F 2013/530481* (2013.01); *C08F 20/06* (2013.01); *C08F 20/18* (2013.01); *C08F 2810/20* (2013.01); *C08J 2300/14* (2013.01); *C08J 2333/02* (2013.01)

(58) Field of Classification Search
CPC ........ C08F 220/08; C08F 20/18; C08F 20/06; C08L 33/08
See application file for complete search history.

(56) References Cited

U.S. PATENT DOCUMENTS

| 5,837,789 | A | 11/1998 | Stockhausen et al. |
| 7,833,624 | B2 | 11/2010 | Harren et al. |
| 2004/0214946 | A1 | 10/2004 | Smith et al. |
| 2006/0029782 | A1* | 2/2006 | Harren ............... A61L 15/60 428/212 |
| 2006/0057389 | A1 | 3/2006 | Reimann et al. |
| 2006/0073969 | A1* | 4/2006 | Torii ............... A61L 15/60 502/400 |
| 2006/0204755 | A1 | 9/2006 | Torii et al. |
| 2007/0078231 | A1 | 4/2007 | Shibata et al. |
| 2007/0100304 | A1* | 5/2007 | Fell ............... A61F 13/15658 604/359 |
| 2008/0032888 | A1 | 2/2008 | Nakamura et al. |
| 2008/0075937 | A1 | 3/2008 | Wada et al. |
| 2009/0131255 | A1 | 5/2009 | Ikeuchi et al. |
| 2009/0215617 | A1 | 8/2009 | Kimura et al. |
| 2011/0319518 | A1 | 12/2011 | Kadonaga et al. |
| 2014/0031473 | A1 | 1/2014 | Nogi et al. |
| 2015/0225514 | A1 | 8/2015 | Kimura et al. |
| 2016/0199527 | A1 | 7/2016 | Ota et al. |

(Continued)

FOREIGN PATENT DOCUMENTS

| CN | 1747751 A | 3/2006 |
| EP | 3067370 A1 | 9/2016 |

(Continued)

OTHER PUBLICATIONS

Extended European Search Report including Written Opinion for Application No. EP17763459.9 dated Dec. 21, 2018.
Search report from International Application No. PCT/KR2017/000055, dated Apr. 11, 2017.
Odian, George, "Principles of Polyermization." Second Edition, (Wiley, 1981), p. 203.
Schwalm, Reinhold, "UV Coatings: Basics, Recent Developments and New Applications." Elsevier Science, Dec. 21, 2006, p. 115.
Patent Cooperation Treaty Third Party Observation, dated Aug. 13, 2018 for International Application No. PCT/KR2017/000055, filed Jan. 3, 2017, 10 pages.

(Continued)

*Primary Examiner* — Mark S Kaucher
(74) *Attorney, Agent, or Firm* — Lerner, David, Littenberg, Krumholz & Mentlik, LLP

(57) ABSTRACT

The present invention relates to a super absorbent polymer which maintains excellent absorption performance and retains physical properties even after being physically damaged by an external force. The super absorbent polymer comprises: a base polymer powder including a first cross-linked polymer of a water-soluble ethylenically unsaturated monomer having at least partially neutralized acidic groups; and a surface cross-linked layer formed on the base polymer powder and including a second cross-linked polymer in which the first cross-linked polymer is further cross-linked via an alkylene carbonate having 2 to 5 carbon atoms, wherein the super absorbent polymer satisfies predetermined physical properties.

14 Claims, No Drawings

(56) References Cited

U.S. PATENT DOCUMENTS

| | | |
|---|---|---|
| 2016/0214082 A1 | 7/2016 | Lee et al. |
| 2016/0271584 A1 * | 9/2016 | Lee .................. B01J 20/3021 |
| 2017/0073478 A1 | 3/2017 | Joo et al. |
| 2017/0361305 A1 | 12/2017 | Kim et al. |

FOREIGN PATENT DOCUMENTS

| | | |
|---|---|---|
| EP | 3101038 A1 | 12/2016 |
| EP | 3345958 A1 | 7/2018 |
| JP | 2001137704 A | 5/2001 |
| JP | 4739682 B2 | 8/2011 |
| JP | 2012007062 A | 1/2012 |
| JP | 5041807 B2 | 10/2012 |
| JP | 2013133399 A | 7/2013 |
| JP | 5362212 B2 | 12/2013 |
| JP | 2014079324 A | 5/2014 |
| KR | 20070012731 A | 1/2007 |
| KR | 20070037423 A | 4/2007 |
| KR | 100876827 B1 | 1/2009 |
| KR | 20150020030 A | 2/2015 |
| KR | 20150056572 A | 5/2015 |
| KR | 20150064712 A | 6/2015 |
| KR | 20160004967 A | 1/2016 |
| KR | 20160016645 A | 2/2016 |
| KR | 20160016714 A | 2/2016 |
| WO | 2000010619 A1 | 3/2000 |
| WO | 2004069293 A1 | 8/2004 |
| WO | 2005025628 A1 | 3/2005 |
| WO | 2010100936 A1 | 9/2010 |
| WO | 2012102407 A1 | 8/2012 |
| WO | 2014167040 A1 | 10/2014 |
| WO | WO-2015084059 A1 * | 6/2015 ................ C08F 2/48 |

OTHER PUBLICATIONS

Chinese Search Report for Application No. CN 201780003839.2 dated Apr. 10, 2020, 2 pages.

* cited by examiner

SUPER ABSORBENT POLYMER

CROSS-REFERENCE TO RELATED APPLICATION(S)

The present application is a national phase entry under 35 U.S.C. § 371 of International Application No. PCT/KR2017/000055, filed on Jan. 3, 2017, which claims the benefit of Korean Patent Application No. 10-2016-0029831, filed on Mar. 11, 2016, and Korean Patent Application No. 10-2016-0104933, filed on Aug. 18, 2016, the disclosures of which are incorporated herein by reference.

TECHNICAL FIELD

The present invention relates to a super absorbent polymer which maintains excellent absorption performance and retains excellent physical properties even after being physically damaged by an external force.

BACKGROUND

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of various products, for example, hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. For these applications, the super absorbent polymer should exhibit a high moisture absorbency, it should not release the absorbed water even in the external pressure, and additionally it should well retain the shape even in a state where the volume is expanded (swelled) by absorbing water, and thereby exhibit excellent liquid permeability.

In particular, in recent years, as studies have been conducted to provide diapers exhibiting excellent performance while having a thinner thickness and a light weight, much attention has been focused on providing a super absorbent polymer having more improved liquid permeability. In order to satisfy the above technical requirements, however, it is necessary that the content of pulp decreases and the content of super absorbent polymer increases. In this case, the liquid permeability that urine is evenly dispersed in the absorber core of the diaper must be more excellent.

In addition, in sanitary materials such as diapers, in which the pulp content is decreased and the content of the super absorbent polymer is increased as described above, there is a greater risk that the super absorbent polymer inside the absorbent core will be physically damaged by external forces not only in the process of manufacture and use but also in the process of packaging, transportation, etc. Therefore, even after being physically damaged by an external force, a super absorbent polymer exhibiting excellent liquid permeability and absorption performance is required.

On the other hand, various attempts have been made to improve the liquid permeability of the super absorbent polymer, and as a representative example thereof, there may be mentioned a method of adding, to the surface cross-linked super absorbent polymer, a water-soluble polyvalent metal compound, an insoluble inorganic fine particle, a cationic polymer compound or the like as an additive for improving the liquid permeability.

However, even with the method according to such criteria, improvement of the liquid permeability of the super absorbent polymer was not sufficient, and furthermore, the additive can be detached from the surface of the super absorbent polymer particles with the lapse of time. Therefore, when the super absorbent resin was physically damaged by an external force, it was often difficult to maintain physical properties such as excellent liquid permeability.

Therefore, there is a continuing need to develop a technique capable of providing a super absorbent polymer which has more improved liquid permeability while maintaining excellent absorption performance, and furthermore, retains physical properties even after being physically damaged by an external force.

Technical Problem

The present invention provides a super absorbent polymer which maintains excellent absorption performance and retains physical properties even after being physically damaged by an external force.

Technical Solution

The present invention provides a super absorbent polymer comprising:

a base polymer powder including a first cross-linked polymer of a water-soluble ethylenically unsaturated monomer having at least partially neutralized acidic groups; and a surface cross-linked layer formed on the base polymer powder and including a second cross-linked polymer in which the first cross-linked polymer is further cross-linked via an alkylene carbonate having 2 to 5 carbon atoms, wherein the super absorbent polymer has the following features:

an EFFC represented by the following Formula 1 is 25 to 30 g/g, a saline flow conductivity (SFC) for a physiological saline solution (0.685 wt % sodium chloride aqueous solution) ($\cdot 10^{-7}$ cm$^3$·s/g) is 100 to 130 ($\cdot 10^{-7}$ cm$^3$·s/g), and a SFC ($\cdot 10^{-7}$ cm$^3$·s/g) measured after crushing the super absorbent polymer powder by a crushing method using a paint shaker is 70 to 100 ($\cdot 10^{-7}$ cm$^3$·s/g).

$$EFFC=(CRC+AUP)/2 \qquad \text{[Formula 1]}$$

in Formula 1,

CRC represents a centrifuge retention capacity for a physiological saline solution (0.9 wt % sodium chloride aqueous solution) of the super absorbent polymer for 30 minutes, and AUP represents an absorbency under pressure under 0.7 psi for a physiological saline solution (0.9 wt % sodium chloride aqueous solution) of the super absorbent polymer for 1 hour.

The present invention also provides a super absorbent polymer comprising:

a base polymer powder including a first cross-linked polymer of a water-soluble ethylenically unsaturated monomer having at least partially neutralized acidic groups;

a surface cross-linked layer formed on the base polymer powder, and including a second cross-linked polymer in which the first cross-linked polymer is further cross-linked via an alkylene carbonate having 2 to 5 carbon atom; and hydrophobic silica particles that are dispersed on the surface cross-linked layer and have a water-contact angle of more than 10°, wherein the super absorbent polymer has the following features:

an EFFC represented by Formula 1 is 25 to 30 g/g, and an EFFC measured after crushing the super absorbent polymer powder by a crushing method using a paint shaker is 25 to 30 g/g.

Hereinafter, the super absorbent polymer according to specific embodiments of the invention will be described in more detail. However, this is merely presented as an example of the present invention, and will be apparent to those skilled in the art that the scope of the present invention is not limited to these embodiments, and various modifications can be made to the embodiments within the scope of the present invention.

In addition, unless stated otherwise throughout this specification, the term "comprises" or "contains" means to include any constituent element (or constituent component) without particular limitation, and it cannot be interpreted as a meaning of excluding an addition of other constituent element (or constituent component).

According to one embodiment of the present invention, there is provided a super absorbent polymer comprising:

a base polymer powder including a first cross-linked polymer of a water-soluble ethylenically unsaturated monomer having at least partially neutralized acidic groups; and a surface cross-linked layer formed on the base polymer powder and including a second cross-linked polymer in which the first cross-linked polymer is further cross-linked via an alkylene carbonate having 2 to 5 carbon atoms, wherein the super absorbent polymer has the following features:

an EFFC represented by the following Formula 1 is 25 to 30 g/g, a saline flow conductivity (SFC) for a physiological saline solution (0.685 wt % sodium chloride aqueous solution) ($\cdot 10^{-7}$ cm$^3$·s/g) is 100 to 130 ($\cdot 10^{-7}$ cm$^3$·s/g), and a SFC ($\cdot 10^{-7}$ cm$^3$·s/g) measured after crushing the super absorbent polymer powder by a crushing method using a paint shaker is 70 to 100 ($\cdot 10^{-7}$ cm$^3$·s/g).

$$EFFC=(CRC+AUP)/2 \quad [\text{Formula 1}]$$

in Formula 1,

CRC represents a centrifuge retention capacity for a physiological saline solution (0.9 wt % sodium chloride aqueous solution) of the super absorbent polymer for 30 minutes, and AUP represents an absorbency under pressure under 0.7 psi for a physiological saline solution (0.9 wt % sodium chloride aqueous solution) of the super absorbent polymer for 1 hour.

According to another embodiment of the present invention, there is provided a super absorbent polymer comprising:

a base polymer powder including a first cross-linked polymer of a water-soluble ethylenically unsaturated monomer having at least partially neutralized acidic groups;

a surface cross-linked layer formed on the base polymer powder and including a second cross-linked polymer in which the first cross-linked polymer is further cross-linked via an alkylene carbonate having 2 to 5 carbon atom; and hydrophobic silica particles that are dispersed on the surface cross-linked layer and have a water-contact angle of more than 10°, wherein the super absorbent polymer has the following features:

an EFFC represented by Formula 1 is 25 to 30 g/g, and an EFFC measured after crushing the super absorbent polymer powder by a crushing method using a paint shaker is 25 to 30 g/g.

The present inventors have conducted continuous research to prepare and provide a super absorbent polymer which further improves a liquid permeability of the super absorbent polymer and retains physical properties even after being physically damaged by an external force. As a result, the inventors have found that, as the base polymer powder having a high gel strength is obtained by optimizing the conditions of the production process of the super absorbent polymer, for example, the type and content of an internal crosslinking agent and the polymerization conditions to be described later, and the surface crosslinking proceeds under specific surface crosslinking conditions (for example, specific silica particles, more specifically, hydrophobic and/or hydrophilic silica particles are used simultaneously or separately during surface crosslinking, etc.), it is possible to provide a super absorbent polymer which maintains excellent absorption performance while exhibiting greatly improved liquid permeability compared to those previously known.

Particularly, as specific hydrophobic silica particles defined by a predetermined contact angle range, more suitably hydrophilic and hydrophobic silica particles, are used together during surface crosslinking, and the surface crosslinking progresses under a constant temperature-raising condition or the like, it is considered that the surface cross-linked layer having a certain level or more of thickness can be evenly formed on the base polymer powder having a high gel strength.

This is presumably because the hydrophilic and hydrophobic silica particles are contained in the second cross-linked structure of the surface cross-linked layer, thereby further tightening the cross-linked structure, and also the surface crosslinking reaction appropriately occurs around the respective silica particles under the temperature-raising condition at the time of surface crosslinking, thereby forming a proper second cross-linked polymer.

Thus, since the surface cross-linked layer can further increase the gel strength of each of the super absorbent polymer particles, the super absorbent polymer according the embodiments of the invention can exhibit greatly improved liquid permeability that is defined as SFC of 100 to 130 ($\cdot 10^{-7}$ cm$^3$·s/g) together with high strength. In addition, the super absorbent polymer according to embodiments of the invention can maintain excellent absorption performance defined by an EFFC of 25 to 30 g/g (arithmetic average value of CRC and AUP) as the internal cross-linked structure and the surface cross-linked structure thereof is optimized.

Furthermore, as the super absorbent polymer has a high gel strength and the silica particles for improving the liquid permeability are used at the time of surface crosslinking and contained on the surface cross-linked layer, the super absorbent polymer can retain excellent physical properties such as liquid permeability and absorption performance, even after physical damage, because the physical damage due to an external force (for example, crushing occurring during the process transfer includes crushing resulting from impact occurring between the super absorbent polymers, impact between the transfer line and the polymer, impact due to pressure during packaging, etc.) is not relatively large, and also there is little fear of detachment of the silica particles.

Therefore, as the super absorbent polymer according to embodiments of the invention exhibits greatly improved liquid permeability and superior absorption performance than those previously known and retains these physical properties even after being physically damaged by an external force, and thus can be very preferably applied to various sanitary materials such as diapers with a content of pulp decreased.

Meanwhile, in the super absorbent polymer of the respective embodiments, hydrophobic silica particles having a water-contact angle of more than 10°, or more than 10° and 170° or less, more suitably 12° to 170° during surface crosslinking. More suitably, these hydrophobic silica particles can be used together with hydrophilic silica particles having a water-contact angle of 10° or less, or 1 to 10°. Thus, the super absorbent polymer according to embodiments of the invention may further include hydrophobic silica particles and/or hydrophilic silica particles that are dispersed on the surface of the base polymer powder, for example, on the surface cross-linked layer. In this case, "the hydrophobic silica particles or the hydrophilic silica particles are dispersed on the surface cross-linked layer" may mean that these respective silica particles are contained/dispersed in the cross-linked structure of the surface cross-linked layer, or are embedded in the surface of the surface cross-linked layer.

More specifically, the hydrophobic silica particles may be contained and treated in a surface crosslinking liquid, or may be mixed and treated on the base polymer powder before surface crosslinking, as described in more detail below. Thus, such hydrophobic silica particles, for example, at least a part thereof, may be present on the surface of the base polymer powder, for example, in the surface cross-linked layer, and a part thereof may be present in a state of being embedded in the surface of the base polymer powder. In addition, the hydrophilic silica particles may be dispersed on the surface cross-linked layer, and the hydrophilic silica particles may be present in the cross-linked structure of the second cross-linked polymer contained therein, or a part thereof may be present in a state of being embedded in the surface of the base polymer powder.

In this way, since the hydrophobic and/or hydrophilic silica particles are evenly present at least on the surface cross-linking layer, the liquid permeability of the super absorbent polymer can be further improved, and even when an external force is applied in the process of packaging or transporting sanitary materials and thus at least a part of the super absorbent polymer particles are physically damaged or crushed, physical properties such as improved liquid permeability or excellent absorption performance can be continuously maintained.

As the hydrophobic silica particles, one or more of the commercially available hydrophobic silica particles having the contact angle range described above can be used without any particular limitation. More suitably, when the hydrophobic silica particles are incorporated in the surface cross-linking liquid, particles having a contact angle of more than 10° and 50° or less can be used from the viewpoint of dispersibility in a surface crosslinking liquid. Also, when the hydrophobic silica particles are mixed in a solid state with the base polymer powder before the surface crosslinking and subjected to a dry treatment, particles having a contact angle of 50° to 170° or less can be suitably used from the viewpoint of improvement in the liquid permeability. In addition, as the above-mentioned hydrophilic silica particles, one or more of the commercially available water-dispersible silica particles having a contact angle range of 10° or less can be used without any particular limitation.

More specifically, as the hydrophobic silica particles, hydrophobic silica particles available under trade name: DM30S, Aerosil or the like can be suitably used. As the hydrophilic silica particles, water-dispersible silica particles available under trade name: ST-O or ST-AK, etc. may be suitably used, thereby further improving the liquid permeability of the super absorbent polymer according to embodiments of the invention.

The water-contact angle, which distinguishes the hydrophilic and hydrophobic silica particles from each other, can be defined as a water-contact angle of each silica particle measured on a glass substrate.

On the other hand, the super absorbent polymer may have a centrifuge retention capacity (CRC) of 25 to 35 g/g, or 26.5 to 30 g/g, and the centrifuge retention capacity (CRC) measured after crushing the super absorbent polymer powder by a crushing method using a paint shaker may also be 25 to 35 g/g, or 26.5 to 30 g/g.

The crushing method using a paint shaker can be, for example, as follows. A paint shaker is a device that mixes a powder expressing a color and a polymer maintaining a shape with each other using beads at a constant speed, time and force. During operation of this device, a lot of heat may be generated in the device due to friction between the mixing materials and the bead. Using such a device, 50 g of super absorbent polymer particles and 10 g of glass beads (particle size: 3 mm) are put in a glass bottle with a hard wall surface and stirred for 1 hour in a paint shaker. The friction and heat between the super absorbent polymer particles and the wall surface of the processing device can be simulated by friction and heat generated in the stirring process. However, even after carrying out the crushing method using a paint shaker thus simulated, the super absorbent polymer can maintain high centrifuge retention capacity as described above.

As described above, the super absorbent polymer according to embodiments of the invention can exhibit excellent absorbency even after being physically damaged by an external force.

In this case, the centrifuge retention capacity (CRC) for the physiological saline solution can be calculated by the following Calculation Equation 1 after absorbing the super absorbent polymer in a physiological saline solution over a period of 30 minutes.

$$CRC(g/g)=\{[W_2(g)-W_1(g)-W_0(g)]/W_0(g)\}$$ [Calculation Equation 1]

in Calculation Equation 1, $W_0(g)$ is an initial weight(g) of the super absorbent polymer, $W_1(g)$ is a weight of the device not including the super absorbent polymer, measured after soaking the same in a physiological saline solution for 30 minutes and dehydrating the same by using a centrifuge at 250 G for 3 minutes, and $W_2(g)$ is the weight of the device including the super absorbent polymer, measured after soaking the super absorbent polymer in a physiological saline solution at room temperature for 30 minutes, and then dehydrating the same by using a centrifuge at 250 G for 3 minutes.

In addition, the super absorbent polymer may have an absorbency under pressure (AUP) of 24 to 30 g/g, or 24.2 to 26 g/g, and the absorbency under pressure (AUP) measured after crushing the super absorbent polymer powder by a crushing method using a paint shaker may also be 24 to 30 g/g, or 24 to 26 g/g.

The absorbency under pressure (AUP) can be calculated by the following Calculation Equation 2 after absorbing the super absorbent polymer in a physiological saline solution under pressure of 0.7 psi over a period of 1 hour.

$$AUP(g/g)=[W_4(g)-W_3(g)]/W_0(g) \quad \text{[Calculation Equation 2]}$$

in Calculation Equation 2, $W_0(g)$ is an initial weight(g) of the super absorbent polymer, $W_3(g)$ is the total sum of a weight of the super absorbent polymer and a weight of the device capable of providing a load to the super absorbent polymer, and $W_4(g)$ is the total sum of a weight of the super absorbent polymer and a weight of the device capable of providing a load to the super absorbent polymer, after absorbing a physiological saline solution to the super absorbent polymer under a load (0.7 psi) for 1 hour.

As the super absorbent polymer according to embodiments of the invention exhibits the centrifuge retention capacity (CRC) and the absorbency under pressure (AUP) within the above-described range, the super absorbent polymer may have an EFFC represented by the following Formula 1 of 25 to 30 g/g, or 25.5 to 28 g/g. Also, the EFFC measured after crushing the super absorbent polymer powder by a crushing method using a paint shaker may be 25 to 30 g/g, or 25.5 to 28 g/g. As described above, the super absorbent polymer according to embodiments of the invention can exhibit excellent absorption performance such as basic absorbency and absorbency under pressure, and also exhibits high gel strength and crosslinking property. Thus, it can exhibit excellent absorption performance even after being physically damaged or crushed by an external force.

Further, the super absorbent polymer according to embodiments of the invention can have a saline flow conductivity (SFC) for a physiological saline solution of 100 to $130 \cdot 10^{-7}$ cm$^3$·s/g or 102 to $120 \cdot 10^{-7}$ cm$^3$·s/g, and the saline flow conductivity (SFC) for a physiological saline solution measured after crushing the super absorbent polymer powder by a crushing method using a paint shaker may be 70 to $100 \cdot 10^{-7}$ cm$^3$·s/g or 74 to $90 \cdot 10^{-7}$ cm$^3$·s/g. As described above, the super absorbent polymer not only exhibits improved liquid permeability than previously known, but also contains predetermined silica particles or the like in the surface cross-linking layer and thus the surface cross-linked layer having a certain level or more of thickness is evenly formed. Therefore, it can maintain excellent liquid permeability even after being physically damaged or crushed by an external force.

This saline flow conductivity for a physiological saline solution (SFC) can be measured and calculated for the super absorbent polymers before and after crushing according to the method already well-known to those skilled in the art, for example, the method disclosed in paragraphs [0184] to [0189] of Column 16 of U.S. Patent Application Publication No. 2009-0131255.

Meanwhile, the super absorbent polymer according to embodiments of the invention can be provided so as to have a particle size of 150 to 850 μm. Specifically, at least 95% by weight of the super absorbent polymer has a particle size of 150 to 850 μm, a fine powder having a particle size of less than 150 μm may be less than 3% by weight, or less than 1.5% by weight, and large particles having a particle size of more than 850 μm may be less than 2% by weight, or less than 1.8% by weight. More specifically, the super absorbent polymer may include particles having a particle size of 150 to 300 μm in an amount of 10 to 20% by weight, include particles having a particle size of 300 to 600 μm in an amount of 55 to 75% by weight, and include particles having a particle size of 600 to 850 μm in an amount of 10 to 20% by weight.

In addition, since the super absorbent polymer has a high gel strength, at least 95% by weight of the super absorbent polymer has a particle size of 150 to 850 μm, a fine powder having a particle size of less than 150 μm may be less than 4% by weight, or less than 3% by weight, and large particles having a particle size of more than 850 μm may be less than 2% by weight, or less than 1% by weight, even after being crushed by a crushing method using a paint shaker. More specifically, the super absorbent polymer may include particles having a particle size of 150 to 300 μm in an amount of 15 to 25% by weight, include particles having a particle size of 300 to 600 μm in an amount of 55 to 75% by weight, and include particles having a particle size of 600 to 850 μm in an amount of 5 to 15% by weight, even after the crushing.

Small changes in the particle size distribution before and after the crushing can reflect excellent gel strength of the super absorbent polymer according to embodiments of the invention.

Depending on the superior gel strength of the super absorbent polymer, physical damage due to the external force applied during packaging and transferring process of sanitary materials can be small, and even if a part of the super absorbent polymer is physically damaged, a decrease in physical properties can be small.

The super absorbent polymer according to embodiments of the invention can be typically obtained by polymerizing a water-soluble ethylenically unsaturated monomer having at least partially neutralized acidic groups, such as a mixture of acrylic acid and its sodium salt in which at least a part of carboxylic acid is neutralized with sodium salt or the like, in the presence of an internal crosslinking agent. More specifically, the super absorbent polymer can be obtained by carrying out a crosslinking polymerization of the above-mentioned monomer in the presence of an internal crosslinking agent to obtain a base polymer powder, and then surface-crosslinking the base polymer powder in the presence of a predetermined surface crosslinking agent and silica particles to prepare a cross-linked polymer.

More specifically, it has been found that, as the base polymer powder having high gel strength is obtained by adjusting the type and content of an internal crosslinking agent, the polymerization conditions, and the like, and then the surface crosslinking proceeds under specific conditions using specific silica particles, for example, specific hydrophobic silica particles, more suitably hydrophilic and hydrophobic silica particles, thereby preparing a super absorbent polymer according to the respective embodiments exhibiting the above-mentioned various physical properties.

A method for preparing such super absorbent polymer may comprise the steps of:

carrying out a crosslinking polymerization of a water-soluble ethylenically unsaturated monomer having at least partially neutralized acidic groups in the presence of an internal crosslinking agent to form a hydrogel polymer including a first cross-linked polymer;

drying, pulverizing, and classifying the hydrogel polymer to form a base polymer powder; and heat-treating the base polymer powder using a surface crosslinking liquid containing a surface crosslinking agent of an alkylene carbonate having 2 to 5 carbon atoms in the presence of hydrophobic silica particles having a water-contact angle of more than 10° and hydrophilic silica particles having a water-contact angle of 10° or less.

According to this preparation method, the surface crosslinking proceeds by using the above-mentioned hydrophobic silica particles and hydrophilic silica particles and concurrently using a surface crosslinking liquid containing an alkylene carbonate-based surface crosslinking agent during surface crosslinking. This makes it possible to uniformly form a surface cross-linked layer having a certain level or more of a thickness, and to prepare a super absorbent polymer according to the above-mentioned embodiments exhibiting more improved gel strength and liquid permeability, and also maintaining excellent absorption performance and excellent physical properties even after physical damages.

In such super absorbent polymer, the water-soluble ethylenically unsaturated monomer may include at least one selected from the group consisting of anionic monomers of acrylic acid, methacrylic acid, maleic anhydride, fumaric acid, crotonic acid, itaconic acid, 2-acryloylethanesulfonic acid, 2-methacryloylethanesulfonic acid, 2-(meth)acryloylpropanesulfonic acid or 2-(meth)acrylamido-2-methylpropanesulfonic acid, and their salts; non-ionic, hydrophilic group-containing monomers of (meth)acrylamide, N-substituted (meth)acrylate, 2-hydroxyethyl(meth)acrylate, 2-hydroxypropyl(meth)acrylate, methoxypolyethylene glycol (meth)acrylate or polyethylene glycol (meth)acrylate; and amino group-containing unsaturated monomers of (N,N)-dimethylaminoethyl(meth)acrylate or (N,N)-dimethylaminopropyl(meth)acrylamide, and their quaternary product. Among them, acrylic acid and/or a salt thereof, for example, an alkali metal salt such as acrylic acid or a sodium salt thereof having at least partially neutralized acrylic acids can be used, and the use of these monomers enables production of a super absorbent polymer having more excellent physical properties. In the case of using acrylic acid and its alkali metal salt as a monomer, it is possible to use acrylic acid after neutralizing at least a part thereof with a basic compound such as caustic soda (NaOH).

Further, as the internal crosslinking agent for crosslinking the monomer, at least one selected form the group consisting of bis(meth)acrylamide having 8 to 12 carbon atoms, a polyol of poly(meth)acrylate having 2 to 10 carbon atoms, and poly(meth)acrylate having 2 to 10 carbon atoms can be used. More specifically, as the internal crosslinking agent, one or more poly(meth)acrylates selected from the group consisting of polyethylene glycol di(meth)acrylate, polypropyleneoxy di(meth)acrylate, glycerin diacrylate, glycerin triacrylate and trimethylol triacrylate can be suitably used. Among them, as an internal crosslinking agent such as polyethylene glycol di(meth)acrylate is used, the internal crosslinking structure is optimized and a base polymer powder or the like having high gel strength can be obtained, Thereby, the super absorbent polymer satisfying physical properties according to the embodiments of the invention can be more appropriately obtained.

Further, the specific internal crosslinking agent may be used in a ratio of 0.005 mol or more, or 0.005 to 0.1 mol, or 0.005 to 0.05 mol (or 0.3 or more parts by weight, or 0.3 to 0.6 parts by weight relative to 100 parts by weight of acrylic acid) based on 1 mol of the non-neutralized acrylic acid contained in the monomer. According to the content range of the internal crosslinking agent, a base polymer powder having a high gel strength before surface crosslinking can be appropriately obtained, and a super absorbent polymer according to embodiments of the invention can be obtained.

After carrying out a crosslinking polymerization of the monomer using the internal crosslinking agent, processes such as drying, pulverizing and classifying are performed to obtain a base polymer powder. Through the processes such as the pulverizing and classifying, the base polymer powder and the super absorbent polymer obtained therefrom are suitably prepared and provided so as to have a particle size of 150 to 850 μm. More particularly, at least 95% by weight of the base polymer powder and the super absorbent polymer obtained therefrom have a particle size of 150 to 850 μm, and fine powder having a particle size of less than 150 μm can be less than 3% by weight, or less than 1.5% by weight.

By adjusting the particle size distribution of the base polymer powder and the super absorbent polymer within the preferred range, the super absorbent polymer according to embodiments of the invention can more appropriately exhibit the physical properties already mentioned above.

In addition, the super absorbent polymer may comprise a base polymer powder including a first cross-linked polymer prepared by the above-mentioned method, and a surface cross-linked layer including a second cross-linked polymer in which the first cross-linked polymer is further cross-linked by surface crosslinking.

The surface crosslinking for forming the surface cross-linked layer may be performed by adding the hydrophobic silica particles and/or hydrophilic silica particles together with a surface crosslinking agent. More specifically, the hydrophilic silica particles can be used by containing together with a surface crosslinking liquid containing a surface crosslinking agent of an alkylene carbonate having 2 to 5 carbon atoms. The hydrophobic silica particles can be used by containing together with the surface crosslinking liquid, or they can be mixed separately on the base polymer powder before or after the treatment of the surface crosslinking liquid and subjected to dry treatment in consideration of the low dispersibility of the surface crosslinking liquid. Most suitably, the surface crosslinking can be carried out by adding the hydrophobic silica particles, subjecting to dry treatment on the base polymer powder, and then heat-treating the hydrophobic silica particles-added base polymer powder in the presence of the above hydrophilic silica particles, and a surface crosslinking liquid containing a surface crosslinking agent of an alkylene carbonate having 2 to 5 carbon atoms. The hydrophobic and hydrophilic silica particles have been described above, and thus more specific description thereon will be omitted.

Further, more suitable examples of the alkylene carbonate having 2 to 5 carbon atoms which can be used as the surface crosslinking agent include ethylene carbonate, propylene carbonate, or butylene carbonate, and two or more selected among them may be used together.

On the other hand, hereinafter, the method capable of preparing the super absorbent polymer described above will be described in more detail according to respective steps. However, with regard to the monomers, internal crosslinking agent, surface crosslinking agent, silica particles and particle size distribution already described above, duplicating explanation thereon will be omitted, and the remaining process configuration and condition will be described in detail for each step of the process.

The method for preparing the super absorbent polymer may comprise the steps of: forming a hydrogel polymer including a first cross-linked polymer by carrying out a thermal polymerization or photo polymerization of a monomer composition including a water-soluble ethylenically unsaturated monomer, an internal crosslinking agent and a polymerization initiator; drying the hydrogel polymer; pulverizing and classifying the dried polymer to form a base polymer powder; and performing a surface crosslinking of the base polymer powder using the surface crosslinking liquid including a surface crosslinking agent of an alkylene carbonate having 2 to 5 carbon atoms in the presence of hydrophobic and hydrophilic silica particles.

In the above preparation method, the monomer composition includes a water-soluble ethylenically unsaturated monomer, an internal crosslinking agent and a polymerization initiator, and the types of the monomers are the same as those already described above.

Further, in the above composition, the concentration of the water-soluble ethylenically unsaturated monomer may be 20 to 60% by weight, or 40 to 50% by weight based on the entire monomer composition including the respective raw materials and solvents described above, and it may be controlled to be an adequate concentration in consideration of the polymerization time, the reaction conditions or the like. However, when the concentration of the monomer is too low, the yield of the super absorbent polymer is low and there may be a problem with economics. By contrast, when the concentration is too high, there may be problems on the process that some of the monomers may be deposited or the pulverizing efficiency of the prepared hydrogel polymer appears to be low in the pulverizing process, and thus the physical properties of the super absorbent polymer may decrease.

Further, the polymerization initiator is not particularly limited as long as it is an initiator that is generally used in the preparation of the super absorbent polymer.

Specifically, the polymerization initiator may include a thermal polymerization initiator or a photo polymerization initiator by UV irradiation, according to the polymerization method. However, even in the case of photo polymerization method, a thermal polymerization initiator may be additionally included because a certain amount of heat is generated by the irradiation of UV ray and the like, and a certain amount of heat is generated in accordance with the progress of the polymerization reaction, which is an exothermic reaction, and thus, a thermal polymerization initiator may be further included.

The photo polymerization initiator that can be used is not particularly limited by its constitution as long as it is a compound capable of forming a radical by light such as ultraviolet rays.

The photo-polymerization initiator used herein may include, for example, at least one selected from the group consisting of benzoin ether, dialkyl acetophenone, hydroxyl alkylketone, phenyl glyoxylate, benzyl dimethyl ketal, acyl phosphine and α-aminoketone. Meanwhile, specific examples of the acyl phosphine, commercialized lucirin TPO, namely, 2,4,6-trimethyl-benzoyl-trimethyl phosphine oxide may be used. More various photo polymerization initiators are well disclosed in "UV Coatings: Basics, Recent Developments and New Application" written by Reinhold Schwalm, (Elsevier, 2007), p 115, however the example of the photo polymerization initiator is not limited thereto.

The photo polymerization initiator may be included in a concentration of 0.01% to 1.0% by weight based on the monomer composition. When the concentration of the photo polymerization initiator is too low, the polymerization rate may become slow, and when the concentration of the photo polymerization initiator is too high, the molecular weight of the super absorbent polymer becomes small and the physical properties may become uneven.

And, as the thermal polymerization initiator, one or more selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4)_2S_2O_8$), and the like; and examples of the azo-based initiator include 2,2-azobis(2-amidinopropane) dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane]dihydrochloride, 4,4-azobis-(4-cyanovaleric acid) or the like. More various thermal polymerization initiators are well disclosed in "Principle of Polymerization" written by Odian, (Wiley, 1981), p 203, however the example of the thermal polymerization initiator is not limited thereto.

The thermal polymerization initiator may be included in a concentration of 0.001 to 0.5% by weight with respect to the monomer composition. If the concentration of such a thermal polymerization initiator is too low, additional thermal polymerization hardly occurs and the effect due to the addition of the thermal polymerization initiator may be insignificant. If the concentration of the thermal polymerization initiator is excessively high, the molecular weight of the super absorbent polymer may be small and the physical properties may become uneven.

In addition, the types of the internal crosslinking agent contained together with the monomer composition are the same as those already described above. The above internal crosslinking agent may be used in a ratio of 0.01 to 0.5% by weight based on the monomer composition so that the polymerized polymer can be cross-linked. In addition, as already described above, the internal crosslinking agent may be used in a ratio of 0.005 mol or more, or 0.005 to 0.1 mol, or 0.005 to 0.05 mol (or 0.3 or more parts by weight, or 0.3 to 0.6 parts by weight relative to 100 parts by weight of acrylic acid) based on 1 mol of the non-neutralized acrylic acid contained in the monomer. As the internal crosslinking agent is used within such content range, a gel strength range before the surface crosslinking can be suitably achieved. By using the above, the super absorbent polymer more suitably satisfying the physical properties according to one embodiment can be obtained. By using the above, the super absorbent polymer more suitably satisfying the physical properties according to the respective embodiments described above can be obtained.

In addition, the monomer composition may further include additives such as a thickener, a plasticizer, a preservation stabilizer, an antioxidant, and so on, as needed.

The monomer composition may be prepared in the form of solution wherein the raw materials such as the water-soluble ethylenically unsaturated monomer, the photo polymerization initiator, the thermal polymerization initiator, the internal crosslinking agent, and the additives are dissolved in a solvent.

At this time, the above-described solvents can be used without limitation in the constitution as long as they are those which can dissolve said components. For example, one or more solvents selected from the group consisting of water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butylolactone, carbitol, methylcellosolve acetate, and N,N-dimethyl acetamide, and so on may be used alone or in combination.

The solvent may be included in the residual quantity excluding the components disclosed above based on the total content of the monomer composition.

Meanwhile, the method of forming a hydrogel polymer by subjecting such monomer composition to the thermal polymerization or photo polymerization can be used without limitation in the constitution as long as it is a method generally used in the polymerization.

Specifically, the polymerization method is largely classified into the thermal polymerization and the photo polymerization according to the polymerization energy source. Usually, the thermal polymerization may be carried out in the reactor like kneader equipped with agitating spindles, and the photo polymerization may be carried out in the reactor equipped with movable conveyor belt, however the polymerization method disclosed above is only one example, and the present invention is not limited to the polymerization methods disclosed above.

As an example, the hydrogel polymer obtained by subjecting to the thermal polymerization in the reactor like kneader equipped with the agitating spindles disclosed above by providing hot air thereto or heating the reactor may have the size of centimeters or millimeters when it is discharged from the outlet of the reactor, according to the types of the agitating spindles equipped in the reactor. Specifically, the size of the obtained hydrogel polymer can be variously shown according to the concentration of the monomer composition fed thereto, the feeding speed, and the like, and the hydrogel polymer of which the weight average particle size is 2 to 50 mm can be generally obtained.

Further, as described above, when the photo polymerization is carried out in a reactor equipped with a movable conveyor belt, the hydrogel polymer typically obtained may be a hydrogel polymer in a sheet-type having a width of the belt. In this case, the thickness of the polymer sheet may vary according to the concentration of the monomer composition fed thereto and the feeding speed, and the polymer sheet is preferably controlled to have a thickness of 0.5 to 5 cm. If the monomer composition is fed so that the thickness of the sheet-type polymer becomes too thin, the production efficiency becomes low, which is not preferred. If the thickness of the sheet-type polymer exceeds 5 cm, the polymerization reaction may not uniformly occur throughout the thickness of the polymer due to the excessively high thickness.

In this case, the hydrogel polymer thus obtained by the above-described method may have typically a water content of 40 to 80% by weight. Meanwhile, the term "water content" as used herein means a weight occupied by moisture with respect to a total amount of the hydrogel polymer, which may be the value obtained by subtracting the weight of the dried polymer from the weight of the hydrogel polymer. Specifically, the water content is defined as a value calculated by measuring the weight loss according to evaporation of water in the polymer during the drying process of increasing the temperature of the polymer with infrared heating. At this time, the water content is measured under the drying conditions which are determined as follows: the temperature is increased from room temperature to 180° C., then the temperature is maintained at 180° C., and the total drying time is set to 20 minutes, including 5 minutes for the temperature rising step.

Next, the step of drying the hydrogel polymer thus obtained is performed.

If necessary, a coarsely pulverizing step may be performed before the drying step, in order to increase the efficiency of the drying step.

In this case, a pulverizing device used herein may include, but the constitution is not limited to, any one selected from the group consisting of a vertical pulverizing device, a turbo cutter, a turbo grinder, a rotary cutter mill, a cutter mill, a disc mill, a shred crusher, a crusher, a chopper, and a disc cutter, but is not limited thereto.

In this case, the coarsely pulverizing step may be performed so that the hydrogel polymer has a particle size of 2 to 10 mm.

To pulverize the polymer to have a particle size of less than 2 mm is technically not easy due to a high water content of the hydrogel polymer, and a phenomenon of agglomeration may occur between the pulverized particles. Meanwhile, if the polymer is pulverized to have a particle size of larger than 10 mm, the effect of increasing the efficiency in the subsequent drying step may be insignificant.

The hydrogel polymer coarsely pulverized as above or immediately after polymerization without the coarsely pulverizing step is subjected to a drying step. At this time, the drying temperature of the drying step may be 150 to 250° C. When the drying temperature is less than 150° C., there is a concern that the drying time becomes excessively long or the physical properties of the super absorbent polymer finally formed may be deteriorated, and when the drying temperature is higher than 250° C., only the surface of the polymer is excessively dried, and thus there is a concern that fine powder may be generated during the subsequent pulverization process and the physical properties of the super absorbent polymer finally formed may be deteriorated. Therefore, the drying process may be preferably performed at a temperature of 150 to 200° C., and more preferably 160 to 180° C.

Meanwhile, the drying step may be carried out for 20 to 90 minutes, in consideration of the process efficiency, but is not limited thereto.

The drying method of the drying step may be selected and used in the drying step without limitation in the constitution if it can be generally used for drying the hydrogel polymer. Specifically, the drying step may be carried out by a method of supplying hot air, irradiating infrared rays, irradiating microwaves, irradiating ultraviolet rays or the like. When the drying step as above is finished, the water content of the polymer may be about 0.1 to about 10% by weight.

Next, the dried polymer obtained from the drying step is subjected to a pulverizing step.

The polymer powder obtained after the pulverization step may have a particle size of 150 to 850 μm. Specific examples of a milling device that can be used for pulverizing to have the above particle size may include a pin mill, a hammer mill, a screw mill, a roll mill, a disc mill, a jog mill, other mixer type mill, or the like, but the present invention is not limited thereto.

In order to properly control the physical properties of the super absorbent polymer powder finally produced after the pulverization step, a separate classifying step can be performed according to the particle sizes of the polymer powders obtained from the pulverization. Preferably, a polymer having a particle size of 150 to 850 μm is classified and only particle having such particle size is subjected to the surface crosslinking reaction and finally commercialized. The particle size distribution of the base polymer powder obtained through such process has been described above, and thus more specific description thereon will be omitted.

On the other hand, after obtaining the base polymer powder through the pulverizing and classifying steps, the super absorbent polymer can be prepared through the surface crosslinking step. The types of the surface crosslinking agent, the hydrophobic and/or hydrophilic silica particles usable in the surface crosslinking step have been described above, and thus more specific description thereon will be omitted.

Further, as already described above, the hydrophilic silica particles can be included in the surface crosslinking liquid and may be used during the surface crosslinking. The hydrophobic silica particles can be included together in the surface crosslinking liquid according to the degree of hydrophobicity defined by the contact angle thereof and may be used concurrently with the surface crosslinking, or may be separately surface-treated with the base polymer powder before or after the treatment of the surface cross-linking liquid, more preferably before the treatment of the surface crosslinking liquid.

In the separate treatment of the hydrophobic silica particles, hydrophobic silica particles may be mixed in a solid state on the base polymer powder to carry out the surface treatment thereof. The treatment method thereof may be based on a dry process and/or a mixing method of a general inorganic powder.

With regard to the method of adding the surface crosslinking liquid containing the hydrophilic silica particles and the surface crosslinking agent and optionally the hydrophobic silica particles to the base polymer powder, there is no particular limitation in the constitution. For example, a method of adding and mixing the surface crosslinking liquid and the base polymer powder in a reactor, a method of spraying the surface crosslinking liquid onto the base polymer powder, or a method of continuously feeding the base polymer powder and the surface crosslinking liquid to a mixer which is continuously operated, or the like, may be used.

The surface crosslinking liquid may further include water and/or methanol as a medium. Thus, there is an advantage that the surface crosslinking agent and the silica particles can be evenly dispersed on the base polymer powder. In this case, the content of water and methanol can be applied by adjusting the addition ratio with respect to 100 parts by weight of the base polymer powder, for the purpose of inducing the uniform dispersion of the surface crosslinking agent and the silica particles, preventing the phenomenon of aggregation of the base polymer powder and at the same time optimizing the surface penetration depth of the surface crosslinking agent.

The above-mentioned surface crosslinking liquid may contain the hydrophilic and hydrophobic silica particles in an amount of 0.005 to 0.2 part by weight, respectively, based on 100 parts by weight of the base polymer powder, and may include 0.1 to 3 parts by weight of the surface crosslinking agent. In addition, even in the separate treatment of the hydrophobic silica particles, hydrophobic silica particles may be used in an amount equivalent thereto. In consideration of the hydrophilic and hydrophobic silica particles contained in the surface crosslinking liquid and the content of the surface crosslinking agent, water and/or methanol may be contained as a medium in an appropriate content range.

The surface crosslinking reaction can be proceeded by heating the surface crosslinking liquid-added base polymer powder at a maximum reaction temperature of 140° C. to 200° C., or 150° C. to 195° C. for 5 minutes to 60 minutes, or 10 minutes to 50 minutes, or 20 minutes to 45 minutes. More specifically, the surface crosslinking step can be proceeded by subjecting to a heat treatment under the conditions in which the temperature is raised from an initial temperature of 20° C. to 130° C., or 40° C. to 120° C. to the maximum reaction temperature over a period of 10 minutes to 30 minutes, and the maximum temperature is maintained for 5 minutes to 60 minutes.

By satisfying the conditions of such a surface crosslinking step (in particular, the temperature—raising conditions and the reaction conditions at the maximum temperature of the reaction), the super absorbent polymer suitably satisfying the physical properties according to the respective embodiments can be prepared.

A means for raising the temperature for surface crosslinking reaction is not particularly limited. Heating may be performed by providing a heating medium or by directly providing a heat source. In this case, the type of the heating medium applicable herein may be a hot fluid such as steam, hot air, hot oil, or the like, but the present invention is not limited thereto. Further, the temperature of the heating medium provided may be properly controlled, considering the means of the heating medium, the heating rate, and the target temperature. Meanwhile, as the heat source provided directly, an electric heater or a gas heater may be used, but the present invention is not limited to these examples.

The super absorbent polymer obtained according to the above-mentioned method can maintain excellent absorption performance such as centrifuge retention capacity and absorbency under pressure, satisfy more improved liquid permeability and the like, and retain various physical properties such as liquid permeability or absorption performance even after being physically damaged by an external force. Accordingly, it can be suitably used for sanitary materials such as diapers, particularly, ultra-thin sanitary materials having reduced pulp content.

Advantageous Effects

According to the present invention, there may be provided the super absorbent polymer maintaining excellent absorption performance such as a centrifuge retention capacity and an absorbency under pressure, exhibiting more improved liquid permeability, and retaining excellent physical properties even after being physically damaged by an external force applied during packaging or transporting process of sanitary materials.

This super absorbent polymer can be suitably used for sanitary materials such as disposable diapers, particularly ultra-thin sanitary materials with reduced content of pulp.

DETAILED DESCRIPTION OF THE EMBODIMENTS

Hereinafter, the preferred Examples are provided for better understanding of the invention. However, these Examples are given for illustrative purposes only and not intended to limit the scope of the present invention.

In Examples and Comparative Examples, the water-contact angles of hydrophobic silica particles and hydrophilic silica particles were measured as follows.

First, a coating solution in which the hydrophobic silica particles were dispersed in a methylene chloride solvent in the concentration of 5% by weight was used. After spin-coating the coating solution on a wafer, water was dropped onto the coating layer, and the contact angle was measured. The contact angle thus measured is defined as a water-contact angle of the hydrophobic silica particles, and the measured values are shown in Table 1 below.

Further, in the case of hydrophilic silica particles, the water-contact angle was measured in the same manner as in the case of the hydrophobic silica particles, except that a coating liquid dispersed in water at a concentration of 20% by weight was used.

TABLE 1

| Silica particles | Product name | Water contact angle (°) |
|---|---|---|
| Hydrophobic silica particles | Aerosil 200 | 14 |
| Hydrophilic silica particles | ST-O | 3 |

In the following Examples and Comparative Examples, the physical properties of each super absorbent polymer were measured and evaluated by the following methods.

(1) Evaluation of Particle Size

The particle sizes of the base polymer powders and the super absorbent polymers used in Examples and Comparative Examples were measured in accordance with EDANA (European Disposables and Nonwovens Association) recommended test method No. WSP 220.3.

(2) CRC (Centrifuge Retention Capacity)

For the absorbent polymer prepared in Examples and Comparative Examples, the centrifuge retention capacity (CRC) by absorption magnification under a non-loading condition was measured in accordance with EDANA (European Disposables and Nonwovens Association) recommended test method No. WSP 241.3.

That is, after uniformly inserting $W_0(g)$ (about 0.2 g) of each polymer obtained in Examples and Comparative Examples in a nonwoven fabric-made bag and sealing the same, it was soaked in a physiological saline solution composed of 0.9 wt % sodium chloride aqueous solution at room temperature. After 30 minutes, water was removed from the bag by centrifugation at 250 G for 3 minutes, and the weight $W_2(g)$ of the bag was then measured. Further, the same procedure was carried out without using the polymer, and then the resultant weight $W_1(g)$ was measured.

Using the respective weights thus obtained, the CRC(g/g) was determined according to the following Calculation Equation 1.

$$CRC(g/g)=\{[W_2(g)-W_1(g)-W_0(g)]/W_0(g)\} \quad \text{[Calculation Equation 1]}$$

in Calculation Equation 1, $W_0(g)$ is an initial weight(g) of the super absorbent polymer, $W_1(g)$ is a weight of the device not including the super absorbent polymer, measured after soaking the same in a physiological saline solution for 30 minutes and dehydrating the same by using a centrifuge at 250 G for 3 minutes, and $W_2(g)$ is a weight of the device including the super absorbent polymer, measured after soaking the same in a physiological saline solution at room temperature for 30 minutes, and then dehydrating the same by using a centrifuge at 250 G for 3 minutes.

(3) Absorbency Under Pressure (AUP)

For the absorbent polymer prepared in Examples and Comparative Examples, the absorbency under pressure was measured in accordance with EDANA (European Disposables and Nonwovens Association) recommended test method No. WSP 242.3.

First, a 400 mesh stainless steel net was installed in the cylindrical bottom of a plastic having an internal diameter of 60 mm. $W_0(g, 0.90 g)$ of the absorbent polymers prepared in Examples 1-2 and Comparative Examples 1-3 were uniformly scattered on the steel net under conditions of temperature of 23±2° C. and relative humidity of 45%, and a piston which can further provide a load of 4.83 kPa (0.7 psi) uniformly was put thereon. The external diameter of the piston was slightly smaller than 60 mm, there was no gap between the cylindrical internal wall and the piston, and the jig-jog of the cylinder was not interrupted. At this time, the weight $W_3(g)$ of the device was measured.

After putting a glass filter having a diameter of 125 mm and a thickness of 5 mm in a Petri dish having a diameter of 150 mm, a physiological saline solution composed of 0.90 wt % of sodium chloride was poured in the dish until the surface level became equal to the upper surface of the glass filter. A sheet of filter paper having a diameter of 120 mm was put thereon. The measuring device was put on the filter paper and the solution was absorbed under a load for 1 hour. After 1 hour, the weight $W_4(g)$ was measured after lifting the measuring device up.

Using the respective mass fractions thus obtained, AUP (g/g) was calculated according to the following Calculation Equation 2, thereby confirming the absorbency under pressure.

$$AUP(g/g)=[W_4(g)-W_3(g)]/W_0(g) \quad \text{[Calculation Equation 2]}$$

in Calculation Equation 2, $W_0(g)$ is an initial weight(g) of the super absorbent polymer, $W_3(g)$ is the total sum of a weight of the super absorbent polymer and a weight of the device capable of providing a load to the super absorbent polymer, and $W_4(g)$ is the total sum of a weight of the super absorbent polymer and a weight of the device capable of providing a load to the super absorbent polymer, after absorbing a physiological saline solution to the super absorbent polymer under a load (0.7 psi) for 1 hour.

(4) Saline Flow Conductivity (SFC)

The saline flow conductivity was measured in accordance with the method disclosed in paragraphs [0184] to [0189] of Column 16 of U.S. patent application publication no. 2009-0131255.

(5) Physical Property Evaluation after Crushing

After each super absorbent polymer was crushed by the crushing method using a paint shaker as follows, the particle size, CRC, AUP and SFC were evaluated by the above-mentioned method.

First, two 500 ml glass containers were prepared. After taking the super absorbent polymer $W_0$ (100 g) obtained in each of Examples and Comparative Examples, the initial particle size distribution of the polymer powder having a particle size of 150 to 850 μm was measured. The weight $W_1$ (50 g) of the polymer was measured in the same amount as the particle size distribution thus measured, and all was placed in the glass container. Thereafter, glass beads (particle diameter: 3 mm) $W_2$ (10 g) were placed in the glass container. For the structural balance of the paint shaker, two samples could be fixed, so that the same experiment could be performed twice.

The prepared polymer sample was fixed and then stirred in a paint shaker for 1 hour. The particle size of 150 to 850 μm was measured once again for the stirred sample, and the particle size distribution changed based on the initial polymer $W_0$ (100 g) was measured and calculated. After confirming the particle size distribution, all of the samples were collected, and the physical properties were re-measured in accordance with the above-described method.

Example 1

100 g of acrylic acid, 0.5 g of polyethylene glycol diacrylate (Mw=523) as a crosslinking agent, 83.3 g of 50% caustic soda (NaOH), and 89.8 g of water were mixed to prepare a monomer aqueous solution composition having a monomer concentration of 45% by weight.

Subsequently, 810 g of the monomer aqueous solution was first mixed with 30.54 g of a 0.18% ascorbic acid solution and 33 g of a 1% sodium persulfate solution, and the mixture was fed through a feed section of a continuous polymerization reactor with a kneader, together with 30.45 g of a 0.15% hydrogen peroxide solution, so as to perform polymerization. At this time, temperature of the polymerization reactor was maintained at 80° C., and the maximum polymerization temperature was 110° C. and the polymerization time was 1 min and 15 s. Thereafter, kneading was continuously performed, and polymerization and kneading were performed for 20 min. Thereafter, the size of the polymer produced was distributed to less than 0.2 cm. At this time, the water content of the hydrogel polymer finally formed was 51% by weight.

Subsequently, the resulting hydrogel polymer was dried in a hot-air dryer at a temperature of 180° C. for 30 minutes, and the dried hydrogel polymer was pulverized with a pin mill. Then, the polymer having a particle size of less than about 150 μm and the polymer powder having a particle size of about 150 μm to 850 μm were classified using a sieve.

A surface treatment liquid containing 0.02 wt % of hydrophobic silica particles (Aerosil 200), 0.02 wt % of hydrophilic silica particles (ST-O), 1 wt % of ethylene carbonate and 4 wt % of water as a solvent based on the weight of the classified base polymer powder was formed. This surface crosslinking liquid was sprayed onto the base polymer powder, stirred at room temperature, and mixed so that the surface treatment liquid was evenly distributed on the base polymer powder. Then, the base polymer powder was put in a surface crosslinking reactor and the surface crosslinking reaction was carried out.

In the surface crosslinking reactor, it was confirmed that the base polymer powder was gradually heated at an initial temperature near 120° C. After 20 minutes elapsed, operation was performed so as to reach the maximum reaction temperature of 190° C. After reaching the maximum reaction temperature, additional reaction was carried out for 40 minutes, and a sample of the finally produced super absorbent polymer was taken. After the surface crosslinking step, a surface cross-linked super absorbent polymer having a particle size of about 150 μm to about 850 μm was obtained using a sieve.

Example 2

A base polymer powder was prepared in the same manner as in Example 1.

Thereafter, based on the weight of the classified base polymer powder, 0.05 wt % of hydrophobic silica particles (Aerosil 200) was mixed by a method of directly charging in a high-speed mixer, and dry-treated to the base polymer powder. Then, a surface treatment liquid containing 0.02 wt % of hydrophobic silica particles (Aerosil 200), 1 wt % of ethylene carbonate and 4 wt % of water as a solvent based on the weight of the base polymer powder was formed. This surface crosslinking liquid was sprayed onto the base polymer powder, stirred at room temperature, and mixed so that the surface treatment liquid was evenly distributed on the base polymer powder. Then, the base polymer powder was put in a surface crosslinking reactor and the surface crosslinking reaction was carried out.

In the surface crosslinking reactor, it was confirmed that the base polymer powder was gradually heated at an initial temperature near 120° C. After 20 minutes elapsed, operation was performed so as to reach the maximum reaction temperature of 190° C. After reaching the maximum reaction temperature, additional reaction was carried out for 40 minutes, and a sample of the finally produced super absorbent polymer was taken. After the surface crosslinking step, a surface cross-linked super absorbent polymer having a particle size of about 150 μm to 850 μm was obtained using a sieve.

Comparative Example 1

A super absorbent polymer was prepared in the same manner as in Example 1, except that hydrophobic and hydrophilic silica particles were not included in the surface crosslinking liquid.

Comparative Example 2

A super absorbent polymer was prepared in the same manner as in Example 1, except that hydrophobic silica particles were not included in the surface crosslinking liquid.

Comparative Example 3

A super absorbent polymer was prepared in the same manner as in Example 1, except that that hydrophobic and hydrophilic silica particles were not included, and 0.05 wt % of the metal compound containing the polyvalent metal cation of aluminum was included.

For the super absorbent polymers of Examples 1 to 2 and Comparative Examples 1 to 4, the measurement and evaluation of the particle size distribution, CRC, AUP, SFC, and respective physical properties before and after crushing were carried out, and the measured physical property values are shown in Table 2 below. Further, EFFC values of Formula 1 were calculated from the measured CRC and AUP before and after the crushing, and the results are shown together in the following Table 2 below.

TABLE 2

| | | Particle size distribution (μm) | | | | | Physical property | | | |
|---|---|---|---|---|---|---|---|---|---|---|
| | | More than 850 | 600~850 | 300~600 | 150~300 | Less than 150 | CRC (g/g) | AUP (g/g) | EFFC (g/g) | SFC ($10^{-7}$ cm$^3$·s/g) |
| Example 1 | before crushing | 0.08 | 13.24 | 67.88 | 17.71 | 1.1 | 26.7 | 24.6 | 25.7 | 102 |
| | after crushing | 0.02 | 9.5 | 64.5 | 22.67 | 3.31 | 27.0 | 24.7 | 25.9 | 74 |

TABLE 2-continued

|  |  | Particle size distribution (μm) | | | | | Physical property | | | |
|---|---|---|---|---|---|---|---|---|---|---|
|  |  | More than 850 | 600~850 | 300~600 | 150~300 | Less than 150 | CRC (g/g) | AUP (g/g) | EFFC (g/g) | SFC ($10^{-7}$ cm$^3$·s/g) |
| Example 2 | before crushing | 1.67 | 16.03 | 65.36 | 15.47 | 1.47 | 27.0 | 24.2 | 25.6 | 103 |
|  | after crushing | 0.48 | 12.63 | 66.62 | 18.27 | 2.0 | 27.0 | 24.0 | 25.5 | 80 |
| Comparative Example 1 | before crushing | 7.1 | 17.76 | 63.06 | 11.2 | 0.88 | 26.1 | 24.1 | 25.1 | 95 |
|  | after crushing | 1.41 | 12.04 | 67.96 | 16.78 | 1.81 | 25.1 | 22.7 | 23.9 | 69 |
| Comparative Example 2 | before crushing | 1.01 | 12.04 | 65.52 | 20.58 | 0.85 | 26.7 | 24.5 | 25.6 | 90 |
|  | after crushing | 0.45 | 6.90 | 64.91 | 25.44 | 2.30 | 25.8 | 22.3 | 24.1 | 60 |
| Comparative Example 3 | before crushing | 0 | 20.56 | 67.1 | 11.56 | 0.78 | 24.5 | 22.7 | 23.6 | 95 |
|  | after crushing | 0 | 9.77 | 65.2 | 22.13 | 2.9 | 22.5 | 21.5 | 22.0 | 65 |

Referring to Table 2, it was confirmed that the super absorbent polymers of Examples exhibited excellent absorption performance such as EFFC, and excellent and liquid permeability, and further maintained excellent absorption performance and liquid permeability even after physical damage due to an external force.

On the other hand, it was confirmed that the super absorbent polymers of Comparative Examples exhibited poor liquid permeability before and after the crushing or that the absorption performance after crushing was low.

The invention claimed is:

1. A super absorbent polymer comprising:
a base polymer powder including a first cross-linked polymer of a water-soluble ethylenically unsaturated monomer having at least partially neutralized acidic groups; and
a surface cross-linked layer formed on the base polymer powder and including a second cross-linked polymer in which the first cross-linked polymer is further cross-linked via the second cross-linked polymer, where the second cross-linked polymer comprises an alkylene carbonate having 2 to 5 carbon atoms, hydrophilic silica particles having a water-contact angle of 10° or less, and hydrophobic silica particles having a water-contact angle of more than 10°, wherein the hydrophilic and hydrophobic silica particles are dispersed in the surface cross-linked polymer layer,
wherein the super absorbent polymer has the following features:
an EFFC represented by the following Formula 1 is 25 to 30 g/g,
a saline flow conductivity (SFC) for a physiological saline solution (0.685 wt % sodium chloride aqueous solution) (·10$^{-7}$ cm$^3$·s/g) is 100 to 130 (·10$^{-7}$ cm$^3$·s/g), and
a SFC(·10$^{-7}$ cm$^3$·s/g) measured after crushing the super absorbent polymer powder by a crushing method using a paint shaker is 70 to 100(·10$^{-7}$ cm$^3$·s/g), EFFC=(CRC+AUP)/2  [Formula 1]

in Formula 1,
CRC represents a centrifuge retention capacity for a physiological saline solution (0.9 wt % sodium chloride aqueous solution) of the super absorbent polymer for 30 minutes, and
AUP represents an absorbency under pressure under 0.7 psi for a physiological saline solution (0.9 wt % sodium chloride aqueous solution) of the super absorbent polymer for 1 hour.

2. A super absorbent polymer comprising:
a base polymer powder including a first cross-linked polymer of a water-soluble ethylenically unsaturated monomer having at least partially neutralized acidic groups;
a surface cross-linked layer formed on the base polymer powder and including a second cross-linked polymer in which the first cross-linked polymer is further cross-linked via the second cross-linked polymer, wherein the second cross-linked polymer comprises an alkylene carbonate having 2 to 5 carbon atom; and
hydrophobic silica particles having a water-contact angle of more than 10°, and hydrophilic silica particles having a water-contact angle of less than 10°, wherein the hydrophilic and hydrophobic silica particles are dispersed in the surface cross-linked polymer layer,
wherein the super absorbent polymer has the following features:
an EFFC represented by the following Formula 1 is 25 to 30 g/g, and
an EFFC measured after crushing the super absorbent polymer powder by a crushing method using a paint shaker is 25 to 30 g/g, EFFC=(CRC+AUP)/2  [Formula 1]

in Formula 1,
CRC represents a centrifuge retention capacity for a physiological saline solution (0.9 wt % sodium chloride aqueous solution) for 30 minutes, and
AUP represents an absorbency under pressure under 0.7 psi for a physiological saline solution (0.9 wt % sodium chloride aqueous solution) for 1 hour.

3. The super absorbent polymer of claim 1, wherein CRC of the super absorbent polymer is 25 to 35 g/g.

4. The super absorbent polymer of claim 1, wherein AUP of the super absorbent polymer is 24 to 30 g/g.

5. The super absorbent polymer of claim 1, wherein an EFFC measured after crushing the super absorbent polymer powder by a crushing method using a paint shaker is 25 to 30 g/g.

6. The super absorbent polymer of claim 1, wherein the water-soluble ethylenically unsaturated monomer includes at least one selected from the group consisting of anionic monomers, non-ionic, hydrophilic group-containing monomers, and amino group-containing unsaturated monomers and their quaternary product.

7. The super absorbent polymer of claim 1, wherein the first cross-linked polymer includes a polymer in which the monomer is subjected to a crosslinking polymerization in the presence of at least one internal crosslinking agent selected form the group consisting of bis(meth)acrylamide having 8 to 12 carbon atoms, polyol of poly(meth)acrylate having 2 to 10 carbon atoms, and poly(meth)acrylate having 2 to 10 carbon atoms.

8. The super absorbent polymer of claim 1, wherein it has a particle size of 150 to 850 μm.

9. The super absorbent polymer of claim 2, wherein CRC of the super absorbent polymer is 25 to 35 g/g.

10. The super absorbent polymer of claim 2, wherein AUP of the super absorbent polymer is 24 to 30 g/g.

11. The super absorbent polymer of claim 2, wherein the first cross-linked polymer includes a polymer in which the monomer is subjected to a crosslinking polymerization in the presence of at least one internal crosslinking agent selected form the group consisting of bis(meth)acrylamide having 8 to 12 carbon atoms, polyol of poly(meth)acrylate having 2 to 10 carbon atoms and poly(meth)acrylate having 2 to 10 carbon atoms.

12. The super absorbent polymer of claim 6, wherein the anionic monomers is selected from the group consisting of acrylic acid, methacrylic acid, maleic anhydride, fumaric acid, crotonic acid, itaconic acid, 2-acryloylethanesulfonic acid, 2-methacryloylethanesulfonic acid, 2-(meth)acryloyl-propanesulfonic acid or 2-(meth)acrylamido-2-methylpropanesulfonic acid, salts thereof, and mixtures thereof.

13. The super absorbent polymer of claim 6, wherein the non-ionic, hydrophilic group-containing monomers are selected from the group consisting of (meth)acrylamide, N-substituted (meth)acrylate, 2-hydroxyethyl(meth)acrylate, 2-hydroxypropyl(meth)acrylate, methoxypolyethylene glycol(meth)acrylate, polyethylene glycol (meth)acrylate, and mixtures thereof.

14. The super absorbent polymer of claim 6, wherein the amino group-containing unsaturated monomers are selected from the group consisting of (N,N)-dimethylaminoethyl (meth)acrylate, (N,N)-dimethylaminopropyl(meth)acrylamide, their quaternary products thereof, and mixtures thereof.

* * * * *